United States Patent
Ishimaru et al.

(10) Patent No.: US 7,794,492 B2
(45) Date of Patent: Sep. 14, 2010

(54) STENT AND STENT GRAFT

(75) Inventors: Shin Ishimaru, 1-23-23, Jingumae, Shibuya-ku, Tokyo (JP) 150-0001; Yoshihiko Yokoi, Tokyo (JP); Masaaki Matsutani, Tochigi (JP); Yasushi Hashimoto, Tochigi (JP)

(73) Assignees: Kawasumi Laboratories, Inc., Tokyo (JP); Mani Inc., Shioya-gun (JP); Shin Ishimaru, Tokyo (JP)

( * ) Notice: Subject to any disclaimer, the term of this patent is extended or adjusted under 35 U.S.C. 154(b) by 0 days.

(21) Appl. No.: 10/513,336

(22) PCT Filed: May 19, 2003

(86) PCT No.: PCT/JP03/06190

§ 371 (c)(1),
(2), (4) Date: Jun. 10, 2005

(87) PCT Pub. No.: WO03/097155

PCT Pub. Date: Nov. 27, 2003

(65) Prior Publication Data

US 2005/0240257 A1 Oct. 27, 2005

(30) Foreign Application Priority Data

May 20, 2002 (JP) ............................. 2002-144076
Sep. 6, 2002 (JP) ............................. 2002-261519

(51) Int. Cl.
*A61F 2/06* (2006.01)
(52) U.S. Cl. ...................................... 623/1.2; 623/1.13
(58) Field of Classification Search ....... 623/1.13–1.22, 623/1.3–1.32, 1.35; 606/108, 194
See application file for complete search history.

(56) References Cited

U.S. PATENT DOCUMENTS

| 5,609,627 | A | * | 3/1997 | Goicoechea et al. | ......... 128/898 |
| 5,716,393 | A | * | 2/1998 | Lindenberg et al. | .......... 623/1.2 |
| 5,741,333 | A | * | 4/1998 | Frid | ............................ 623/1.2 |
| 5,827,321 | A | * | 10/1998 | Roubin et al. | .............. 623/1.16 |

(Continued)

FOREIGN PATENT DOCUMENTS

| EP | 1177779 A2 * | 2/2002 |
| JP | 3-151983 | 6/1991 |
| JP | 4-126557 | 11/1992 |
| JP | 10-151190 | 6/1998 |
| JP | 11-57020 | 3/1999 |
| JP | 2001-231868 | 8/2001 |

OTHER PUBLICATIONS

U.S. Appl. No. 11/578,287, filed Oct. 13, 2006, Ishimaru, et al.

*Primary Examiner*—Anhtuan T Nguyen
*Assistant Examiner*—Elizabeth Houston
(74) *Attorney, Agent, or Firm*—Oblon, Spivak, McClelland, Maier & Neustadt, L.L.P.

(57) ABSTRACT

A stent formed in a shape of a generally tubular body having a central axis. The stent has a spring function with which the tubular body is diameter-contractible toward the central axis, and the tubular body is expandable to an initial diameter after contraction. The stent maintains a configuration curved along a longitudinal direction of the stent when the stent is not inserted in a sheath. The stent is elongated in a form of a generally straight line along the longitudinal direction when the stent is inserted into the sheath. The stent, being housed in a sheath in the form of a generally straight line, is inserted into a diseased part together with the sheath, is released from the sheath, and radially expands, outwardly after release, to restore and maintain a configuration curved along the longitudinal direction of the stent.

14 Claims, 12 Drawing Sheets

U.S. PATENT DOCUMENTS

| | | | |
|---|---|---|---|
| 6,123,723 A * | 9/2000 | Konya et al. | 623/1.11 |
| 6,270,524 B1 * | 8/2001 | Kim | 623/1.15 |
| 6,432,127 B1 * | 8/2002 | Kim et al. | 623/1.11 |
| 6,554,848 B2 * | 4/2003 | Boylan et al. | 606/191 |
| 6,572,646 B1 * | 6/2003 | Boylan et al. | 623/1.12 |
| 6,827,734 B2 * | 12/2004 | Fariabi | 623/1.18 |
| 6,911,041 B1 * | 6/2005 | Zscheeg | 623/1.15 |
| 2002/0145525 A1 * | 10/2002 | Friedman et al. | 340/573.5 |

* cited by examiner

STENT AND STENT GRAFT

TECHNICAL FIELD

The present invention relates to a stent and a stent graft for use in the treatment of duct-like organs typified by a blood vessel, particularly in the treatment of an aneurysm of the aorta formed in the main artery. The stent and stent graft of the present invention have a configuration that remarkably improves safety and conformity in or to a treatment site of a patient or during the delivery to the treatment site in an artery, etc., and the performance of stable anchoring in a diseased part for a long period of time.

TECHNICAL BACKGROUND

There are many duct-like organs such as a blood vessel, a biliary tract, a urinary tract, a digestive tract, and the like. These duct-like organs may be caused to have characteristic diseases such as a stricture, occlusion, dilation, or the like due to respective various causes. For example, the blood vessel may be caused to have stenosed diseases such as a stricture and occlusion or dilative diseases such as an aneurysm of the aorta and a varix.

Particularly, the aneurysm of the aorta refers to the abnormal dilation of weakened arterial wall caused by hardening or inflammation of the main artery, and it is a critical disease wherein the arterial wall, if left untreated, is gradually dilated from the pressure of a blood flow, and the swelling wall can no longer resist the blood pressure to burst. It therefore requires an immediate treatment or procedure for preventing the bursting and bleeding.

In recent years, a tubular device made of a metal called a stent is often used when an abnormal stenosed part or dilated part of a blood vessel is treated, since no excess invasion such as a surgical operation is required. For example, when an aneurysm of the aorta is treated, the treatment is conducted in such a manner that a stent graft, a device, obtained by covering the above mentioned stent with a tubular member made of a synthetic resin, is used as an artificial blood vessel, and the stent graft is placed within the aneurysm to allow the blood to flow inside the artificial blood vessel, so that the blood pressure is not exerted directly on the swelling wall.

As a stent, conventionally, some types of stents have been provided. Of these, there is used a tubular device obtained by bending a linear material (wire) made of a metal typified by stainless steel to form zigzag patterns, forming the top portion thereof into the form of a curve or curved line, connecting both ends of the linear material to form it into an annular unit, arranging such annular units in series and connecting them with connection struts. It is also another practice to constitute a tubular device from a metal mesh.

For example, when the stent is anchored or placed in a treatment site (diseased part), the stent or stent graft generally inserted in a sheath is restrained, diameter-contracted and loaded into a delivery kit such as a pipe-like cylindrically formed catheter through the inside of which a guide wire is placed. It is introduced into a blood vessel from an incision of a peripheral artery of joint of a leg along the guide wire and delivered to a treatment site such as an aneurysm of the aorta, and when it reaches the treatment site, the above delivery kit is released to remove the contraction of the stent or the like. The stent released from the contraction expands in diameter by itself, and in this state, it is placed or left in a diseased part inside the blood vessel thereby to protect the blood vessel. However, it has been found that the above conventional stent or stent graft (to be sometimes simply referred to as "stent or the like" hereinafter) has the following problems.

(1) The above mentioned stent or the like is basically formed of a tubular body made of a linear metal framework before it is inserted in a sheath. The stent or the like of the above type is to some degree improved in conformity after inserted in a diseased part, by means of design change on configuration or form of the metal framework as required. However, it is composed of a linear tubular body as a basic structure, it exhibits poor conformity to a bent portion of the main artery, so that the deformation of the stent and the damage of the blood vessel are liable to be produced with the passage of time or after a long period of time.

(2) Meanwhile, with a stent graft of a metal mesh type which is manufactured to gain improved flexibility, to be sure, it shows good flexibility and improved conformity. However, the problem is that when the stent is diameter-contracted, the total length thereof increases accordingly, thereby making its positioning for placing the same in the diseased part difficult, the stent-placed position moves or drifts after a long period of time following an operation, or the stent is liable to suffer a structure change with the passage of time, such as deformation, etc., caused by the expansion of the stent toward an aneurysm side.

(3) Further, in case of a tubular body stent formed by connecting annular units having the same diameter and the same number of zigzag patterns, there is no problem to be in the form of a straight line so long as it is not bent. When it is bent, however, from the form of a straight line to a curved form, all of central curved portions nearly face or oppose to each other, or central curved portions and inside spaces between curved portions face or opposed to each other, on the inside of curved line R of the stent. Therefore, i) when the central curved portions of adjacent annular units of a stent face each other, and when the stent is bent, the central curved portions on the inside of the curved line R of the stent overlap and touch each other, so that the stent comes to have difficulties in keeping flexibility and durability.

ii) on the other hand, when the central curved portion of an annular unit of a stent and the inside space of the curved portion of an adjacent unit of the stent face each other, and when the stent is curved, the connection portion and the generally straight line portion are not aligned in generally straight line, so that the stent is liable to be kinked when the annular units connected in the form of a curve are contracted or are restored from contraction, and the stent is liable to be deformed with the passage of time.

Thus the prior stent formed by arranging annular units composed of zigzag patterns each and connected in a linear structure is, in principle, not suitable for bending to make a curved form as described above.

(4) There may be employed a constitution in which the connection portion between the annular units is so arranged to have a larger length than the generally straight line portion that the zigzag patterns do not overlap and touch. However, in this constitution, undesirably, the connection portion may be kinked or suffer torture after a long period of time, or the above constitution may result in insufficient expansion force of the connection portion against a diseased part.

In the light of importance of the above problems of the conventional stent, etc., particularly, for providing a stent that is remarkably improved in safety and conformity during delivery within an artery, or the like, and with the performance of stable anchoring or placing at a diseased part for a long period time, the present inventors have made diligent studies and as a result have arrived at the present invention.

DISCLOSURE OF THE INVENTION

The present invention has been made from the above viewpoint, and according to the present invention, the following invention is provided.

[1] A stent 1 formed in the shape of a generally tubular body, said tubular body having a central axis C, said stent having a spring function with which said tubular body being diameter-contractible toward the central axis C of said tubular body, said tubular body being expandable to the initial diameter after contraction, the stent being loaded and housed in a sheath and being delivered to a diseased part to be treated, wherein (A) said stent 1 maintaining a configuration curved along the longitudinal direction of said stent when the stent is not inserted in the sheath, (B) said stent 1 is being contracted toward the central axis (C) of the stent 1 and is being elongated in the form of a generally straight line along the longitudinal direction of the stent 1 when the stent 1 is inserted into said sheath, whereby the stent 1 is being loaded and housed in the sheath in the form of a generally straight line, and (C) said stent 1, being housed in the sheath in the form of a generally straight line, is being inserted into a diseased part together with the sheath, is being released from the sheath, and radially expanding outwardly after release, to restore and maintain the configuration curved along the longitudinal direction of the stent.

[2] The stent 1 as recited in [1], wherein the stent 1 comprises generally V-letter-shaped zigzag patterns 7 having at least one central curved portion 8, 8A, 8B and generally straight line portions 6, 61, 62, 63, 64 substantially same in length on both sides thereof, the zigzag patterns 7 being formed by repeatedly bending a portion between two ends of a wire base material made of a metal, a plurality of said zigzag patterns 7 are being arranged to surround the central axis C of the stent 1, an annular unit 4A, 4B is being formed by bonding end portions of said wire metal at least in one portion, and a plurality of such annular units 4A, 4B are being constituted, a plurality of said annular units 4A, 4B constituted are being arranged in series in the longitudinal direction (central axis direction) of the stent 1, said annular units 4A, 4B adjacent to each other are being connected to each other with connection struts having substantially the same lengths S each at least in two portions, the struts forming connection portions 5, 5A, 5B, and said generally straight line portions 6, 61, 62, 63, 64 are being formed at a connection angle (θ) of 0°±30° with said connection portions.

[3] The stent 1 as recited in [1] or [2], wherein said strut having at least one annular unit 4A or 4B having an odd number of the zigzag patterns 7 and at least one annular unit 4A or 4B having an even number of the zigzag patterns 7.

[4] The stent 1 as recited in any one of [1] to [3], wherein the annular units 4A, 4B having an odd number of the zigzag patterns 7 and the annular units 4A, 4B having an even number of the zigzag patterns 7 are being disposed to be adjacent to each other and arranged alternately along the longitudinal direction of the stent 1.

[5] The stent 1 as recited in any one of [1] to [4], wherein, in a state where the stent 1 maintains a configuration curved along the longitudinal direction of the stent 1, at least 1 to 4 central curved portions 8, 8A, 8B constituting the zigzag patterns 7 and at least 1 to 4 central curved portions 8, 8A, 8B constituting the zigzag patterns 7 are arranged to be substantially opposed to each other between two connection portions 5, 5A, 5B between two annular units 4A, 4B when viewed from the outermost curved line R side of the stent 1, and the central curved portions 8, 8A, 8B of the zigzag patterns 7 constituting one of the annular units 4A or 4B adjacent to each other and inside spaces 9 of the zigzag patterns 7 of the other of the annular units 4A or 4B are being disposed so that said central curved portions 8, 8A, 8B and inside spaces 9 are substantially facing each other when viewed from the innermost curved line R' side of said stent 1.

[6] The stent 1 as recited in any one of [1] to [5], wherein the connection portions 5, 5A, 5B are of a straight line or a curved line each.

[7] The stent 1 as recited in any one of [1] to [6], wherein the connection portion 5, 5A, 5B having a length s, the generally straight line portion 6, 61, 62, 63, 64 having a length L, and the connection portion 5, 5A, 5B and the generally straight line portion 6, 61, 62, 63, 64 having a ratio of length φ (=S/L) of 0.1 to 2.0.

[8] The stent as recited in any one of [1] to [7], wherein the central curved portion 8, 8A, 8B have a semicircular portion.

[9] The stent 1 as recited in any one of [1] to [8], wherein the generally tubular body under no load is being contracted in diameter by 20% to 90% when said tubular body is inserted into a diseased part.

[10] The stent 1 as recited in any one of [1] to [9], wherein a pipe unit having at least one of functions for reinforcement, marker protection and sustained release of a drug is being fitted to the wire base material made of a metal constituting the tent.

[11] A stent graft formed by covering the stent 1 recited in any one of [1] to [10] with a tubular member 12 made of a synthetic resin.

[12] A stent A' in the form of a generally tubular body comprising generally annular units 2' formed by bonding end. portions of a stent main line 1' made of a metal line wire base material formed in a zigzag form and connection struts 4' connecting said annular units 2' in series, wherein a pipe unit 3' being fitted to a changed portion of the stent main line 1' and/or the connection strut 4' in said annular unit 2' and fixed to said stent main line 1', or a pipe unit 5', 7' being fitted to that portion of the stent main line 1' which is being provided with an element different from the stent main line 1' and/or the strut 4' in said annular unit 2', thereby causing the stent to exhibit at least one of functions for reinforcement, marker protection and sustained release of a drug.

[13] A stent graft comprising the stent A' as recited in [12] and a tubular member 12' made of a synthetic resin covering said stent A'.

BRIEF DESCRIPTION OF DRAWINGS

A more complete appreciation of the invention and many of the attendant advantages thereof will become readily apparent with reference to the following detailed description, particularly when considered in conjunction with the accompanying drawings, in which FIGS. 8-12 are drawings showing another embodiment of a stent and stent graft of the present invention, and in which:

FIG. 1(A) is a schematic drawing (plan view) of the stent of the present invention, and FIG. 1(B) is a partial enlarged view of the zigzag patterns 7;

FIG. 2 is a plan view obtained by viewing the stent in FIG. 1 from X side;

FIG. 3 is a plan view obtained by viewing the stent in FIG. 1 from Y side;

FIG. 4 is a partial enlarged view showing one embodiment of the connection between the connection portion 5 and each substantially straight portion 6 of the stent of the present invention;

FIG. 5 is a schematic drawing showing the state wherein the stent graft of the present invention is contracted;

FIG. 6 is a schematic drawing showing a state wherein the stent graft of the present invention is inserted in a sheath 10 having a curved form at the forward end;

FIG. 7 is a schematic drawing showing a state wherein the stent graft of the present invention is inserted in a sheath 20 having a straight line form at the forward end;

FIG. 8 is a drawing for explaining a stent formed by connecting two annular units with connection struts;

FIG. 9 is a drawing for explaining a structure of welded portion of the stent main line;

FIGS. 10(a) and 10(b) are drawings for explaining a state wherein an X ray impermeable portion 6 is protected with a pipe unit 5';

FIGS. 11(a), and 11(b) and 11(c) are drawings for explaining a state wherein a pipe unit charged with a drug and sealed is attached; and FIGS. 12(a) and 12(b) are drawings for explaining a state where a hook is connected to the stent main line with a pipe unit.

BEST MODE FOR CARRYING OUT THE INVENTION

The present invention will be explained in detail with reference to the drawings hereinafter.

In FIGS. 1-7, 1 indicates a stent, 3 indicates a bonded portion, 4A, 4B, 4C, 4D and 4E indicate annular units, 5, 5A and 5B indicate connection portions or connection struts, 6, 61, 62, 63 and 64 indicate substantially straight line portions, 7 indicates zigzag patterns, 8, 8A and 8B indicate central curved portions, 9 indicate an inside space of the zigzag pattern, 10 and 20 indicate sheaths, 11 indicates a stent graft, 12 indicates a tubular member made of a synthetic resin or a graft, θ indicates a connection angle (formed between the substantially straight line portion and the connection portion), and $\theta_1$, $\theta_2$ and $\theta_3$ indicate angles between annular units.

In FIGS. 8-12, A' indicates a stent, 1' indicates the stent main line, 1a' indicates a welded region, 1b' and 1c' indicate regions adjacent thereto, 1d' indicates a top portion, 2' indicates an annular unit, 3' indicates a pipe unit for reinforcement, 4' indicates a connection strut, 5' indicates a pipe unit for protection, 6' indicates an X ray impermeable portion, 7' indicates a pipe unit for sustained release of a drug, or the like, 7a' indicates a hole portion, 8' indicates a drug or the like, 10' indicates a guide wire, 11' indicates a hook, 12' indicates an annular member or graft made from a synthetic resin, 13 indicates a sheath, 14' indicates a dilator, and 14a' indicates a notched portion.

FIGS. 1 to 4 show the stent of the present invention, and the present invention will be explained first with reference to these drawings.

FIG. 1(A) is a schematic drawing (plan view) that conceptually shows the stent 1 of the present invention, and it shows the form of the stent of the present invention in a load-free state, that is, in a stationary state. FIG. 1(B) is a partially enlarged view of a zigzag pattern 7.

Figure 1:
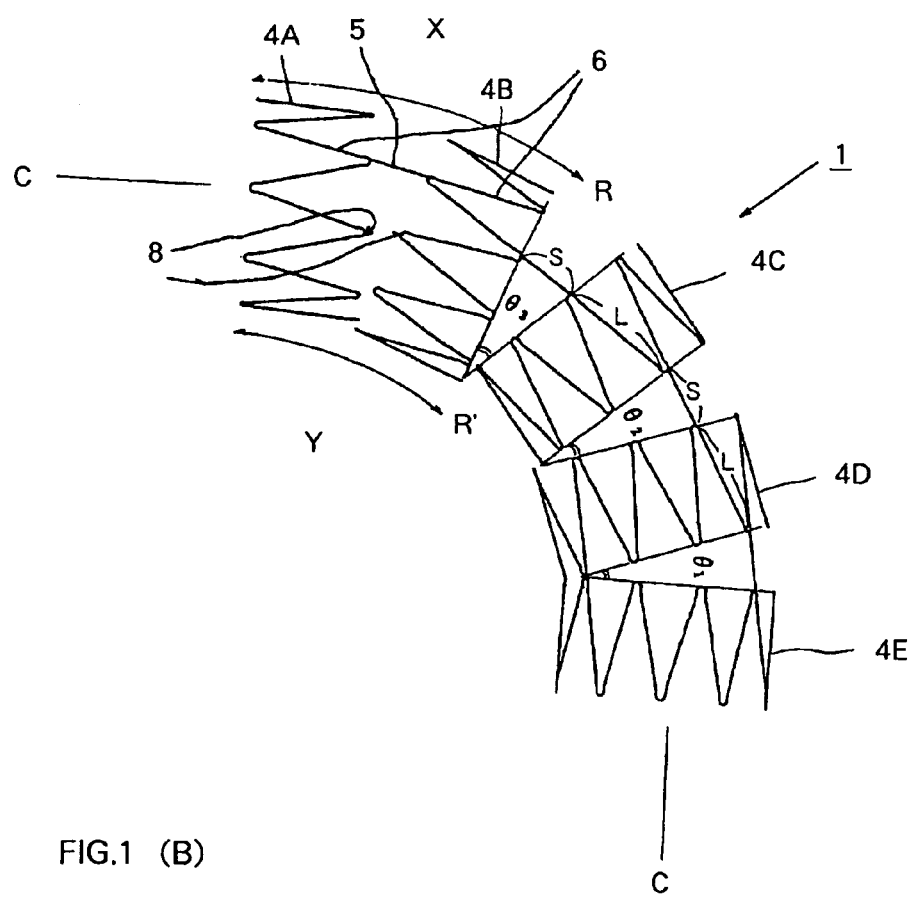
FIGS. 1-7 are drawings showing a stent and stent graft of the present invention.
Figure 1:
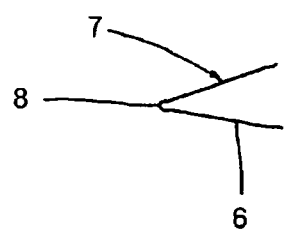
Figure 2:
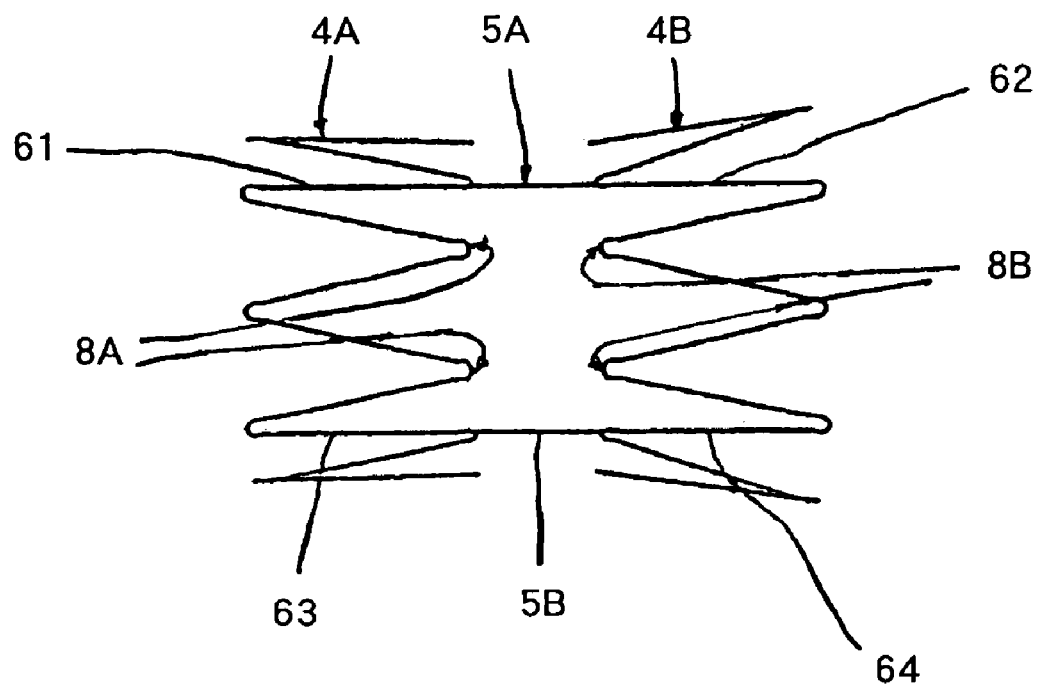

FIG. 2 is a plan view of the stent viewed from X side in FIG. 1, and there is shown one embodiment viewed from the outermost curved line R side of the stent 1, in which two central curved portions 8A of an annular unit 4A constituting zigzag patterns 7 and two central curved portions 8B of an annular unit 4B constituting zigzag patterns 7 are arranged between connection portions 5A and 5B of the two annular units 4A and 4B adjacent to each other, that is, the central curved portions 8A and 8B are arranged between the connection portions 5A and 5B in a state where they are opposed to each other.

Figure 3:
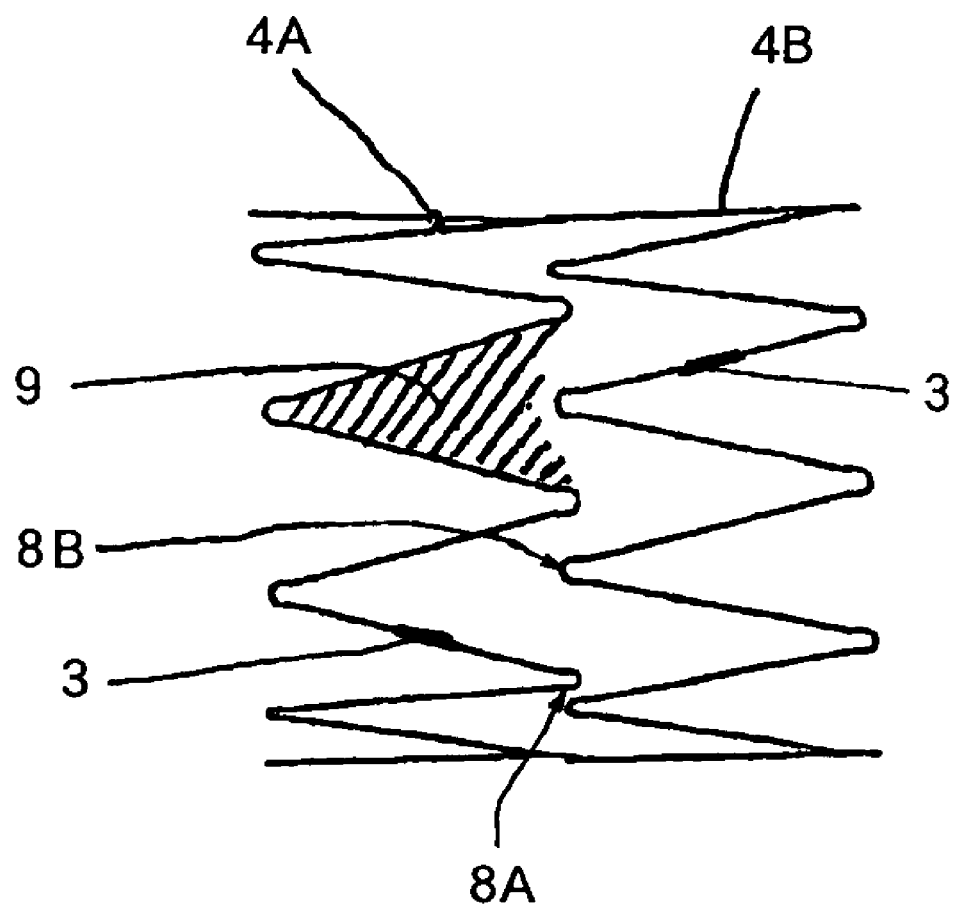

FIG. 3 is a plan view of the stent 1 viewed from Y side in FIG. 1, and there is shown one embodiment viewed from the innermost curved line R' of the stent 1, in which the central curved portions 8A or 8B of the zigzag patterns 7 of the two annular units 4A and 4B and inner spaces 9 of the zigzag patterns 7 are so arranged that they are substantially opposed to each other (they face each other with a close distance between them).

Figure 4:
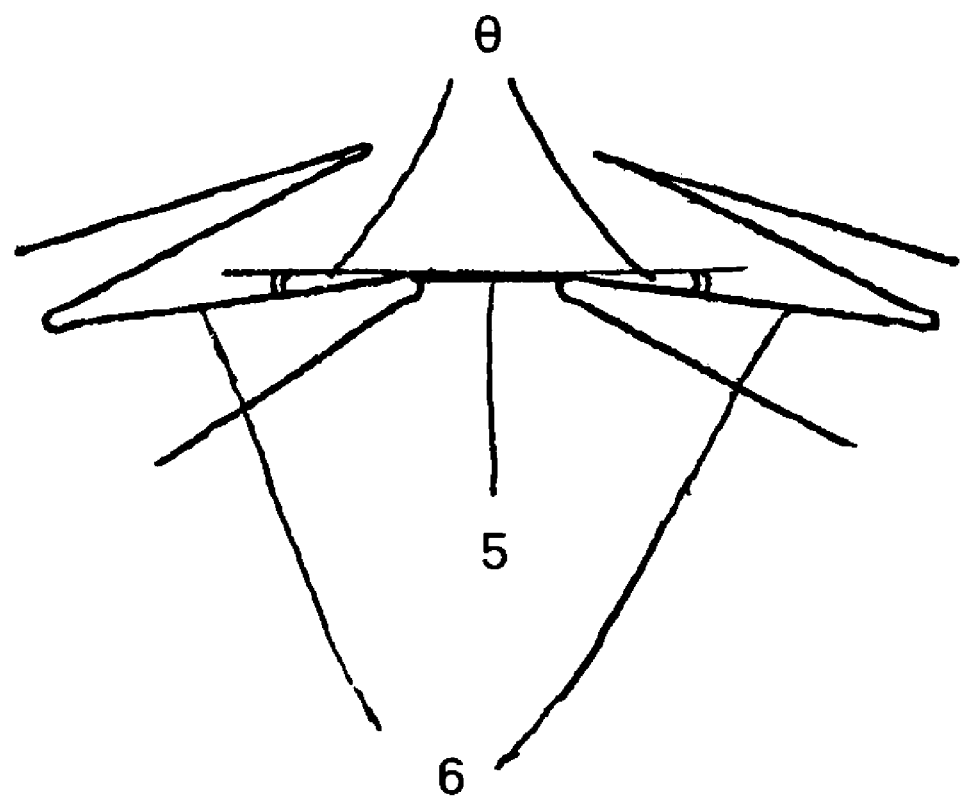

FIG. 4 is a partially enlarged view showing one embodiment of connection of the connection portion 5 (5A, 5B) and generally straight line portions 6 (61, 62, 63, 64).

Figure 5:
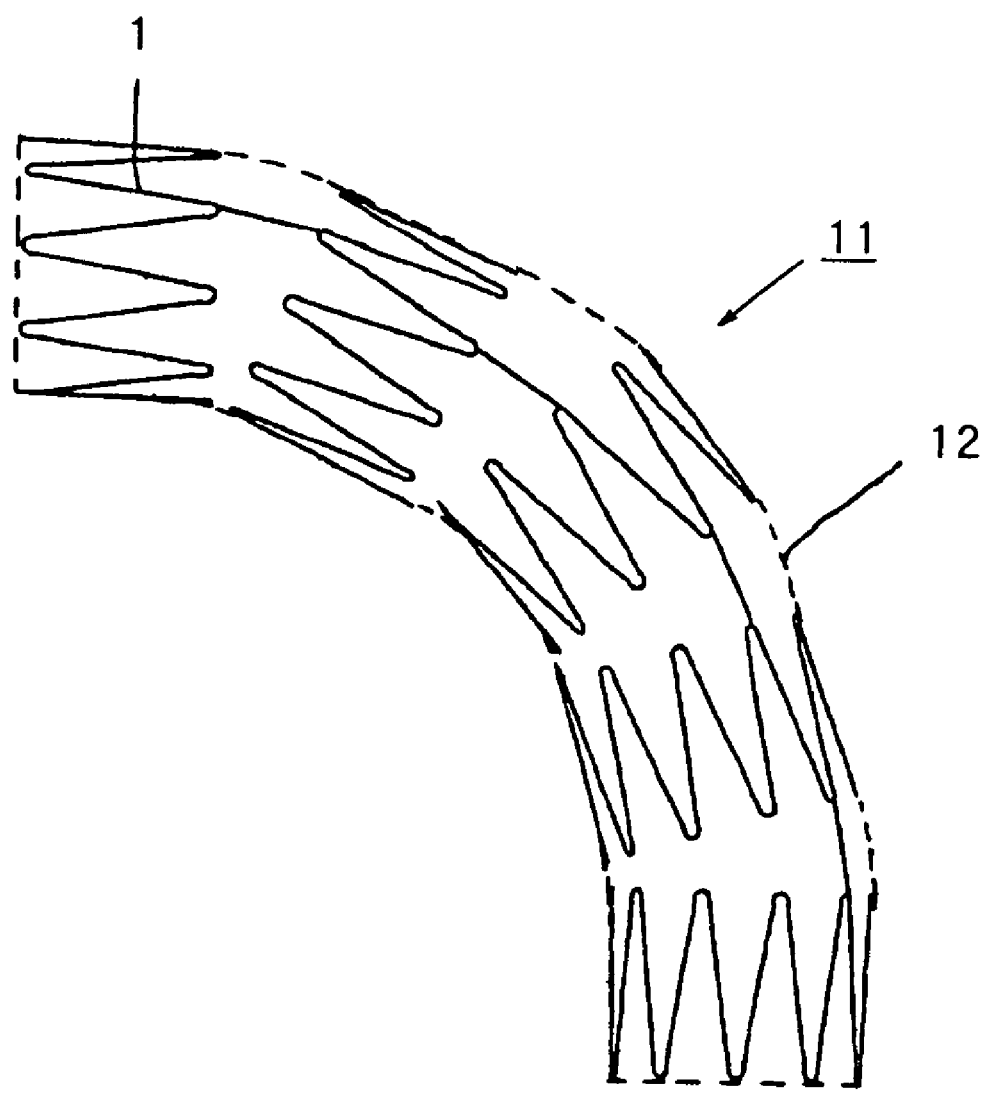
Figure 6:
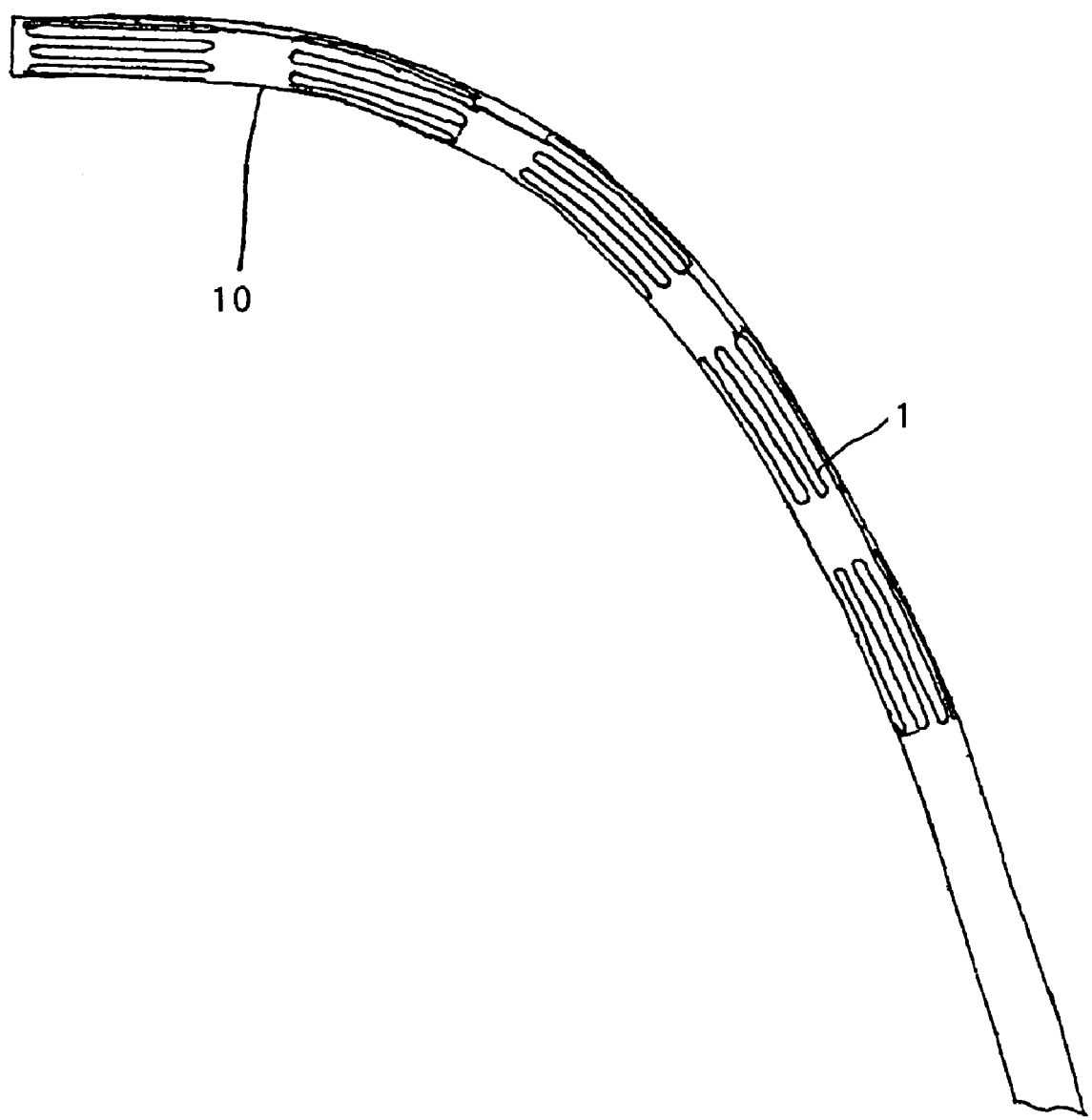

The basic idea of design of the stent 1 of the present invention is as follows. That is, the stent is a stent 1 formed in the shape of a generally tubular body, said tubular body having a central axis C, said stent 1 having a spring function with which said tubular body is diameter-contractible toward the central axis C of said tubular body, said tubular body being expandable to the initial diameter after contraction, the stent 1 is to be loaded and housed in a sheath (sheath member) and is to be delivered to a diseased part to be treated, wherein (A) said stent 1 maintains a configuration curved along the longitudinal direction of said stent 1 as shown in FIG. 1(A) when the stent 1 is not inserted in the sheath, that is, in a stationary state, and (B) when the stent 1 is inserted into said sheath, the stent 1 is contracted toward the central axis C of the stent 1 and is elongated in the form of a generally straight line along the longitudinal direction of the stent 1, whereby the stent 1 is loaded and housed in the sheath, in the form of a generally straight line, or in a curved form as required, as shown in FIGS. 5 and 6, particularly, at the forward end of the sheath, and (C) said stent 1, housed in the sheath in the form of a generally straight line, is being inserted, together with the sheath, into a diseased part, and being released from the sheath, and radially expands outwardly after release, to restore and maintain the curved configuration along the longitudinal direction of the stent, said curved configuration being the stationary state.

In the annular units 4A, 4B and (4C, 4D and 5E) constituting the stent 1 of the present invention, that portion of a wire base material (stent main line) made of a metal which is located between two ends thereof is repeatedly bent to form substantially V-letter-shaped zigzag pattern(s) 7 having at least one central curved portion 8, 8A, 8B and generally straight line portions 6, 61, 62, 63, 64 having substantially the same lengths each on both sides of said central curved portion 8, 8A, 8B, a plurality of such zigzag patterns 7 are cylindrically arranged to surround the central axis C of the stent 1, and each annular unit is formed by bonding and fixing in at least one portion (e.g., portion 3 shown in FIG. 3) of said wire base material made of a metal by known means such as welding, brazing, calking, or the like.

The stent 1 of the present invention has a constitution in which a plurality of the thus-formed annular units 4A, 4B are arranged or extended from one to the other in the longitudinal direction of the stent 1 (that is, in the direction of central axis C) and said adjacent annular units 4A and 4B are connected at least in two portions with connection portions (connection struts) having substantially the same lengths each.

The stent 1 of the present invention can give a three-dimensionally curved or bent shape, according to the form of blood vessels, as shown in FIG. 1, by shifting positions of the above connection portions 5, 5A, 5B between the annular units 4A and 4B.

In the stent 1 of the present invention, the above generally straight line portion 6 (61, 62, 63, 64) is connected to the above connection portion 5 (5A, 5B) at a connection angle θ of 0°±30° as shown in FIG. 4, for readily adjusting the curve angle as required. The above connection angle θ refers to an angle formed between an extending line from the connection portion and the generally straight line portion.

In an embodiment shown in FIGS. 1 and 2, for example, the generally straight line portion 6, 61, 62, 63, 64 adjacent to the left or right side of the connection portion 5, 5A, 5B is connected in the form of a generally straight line (i.e., at a connection angle of 0°). However, when the generally straight line portions 6 are connected symmetrically with regard to the connection portion 5 at a connection angle that is not 0° (−20° to +20°, θ≠0°) as shown in FIG. 4, the curve angle can be adjusted in the connection portion 5, 5A, 5B with a higher degree of freedom, which is more effective against kinking that occurs after a long period of time. FIG. 4 shows an embodiment in which the connection portion 5 and the generally straight line portion 6 are connected to each other at a connection angle θ of 8°.

Figure 8:
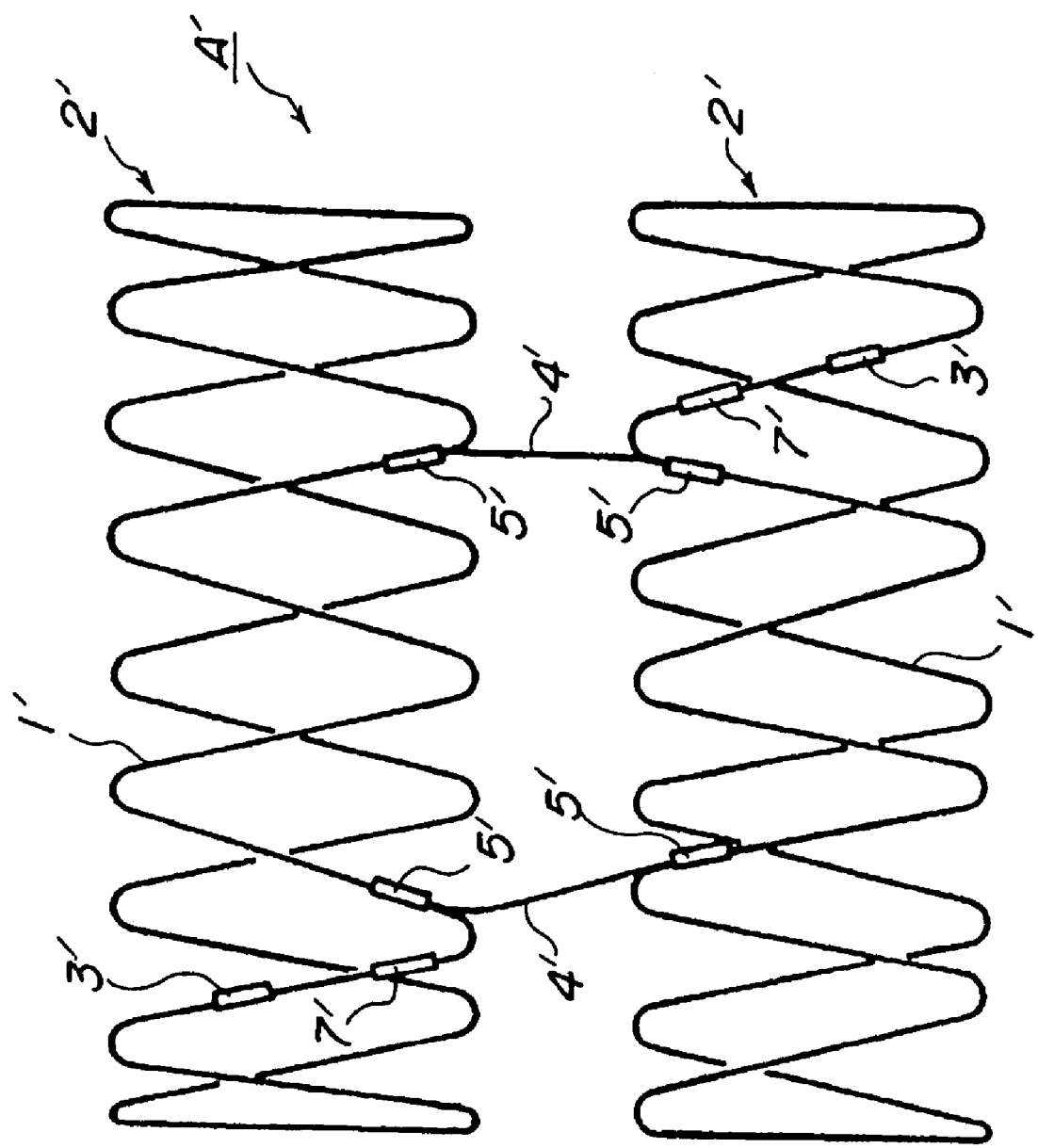
Figure 10:
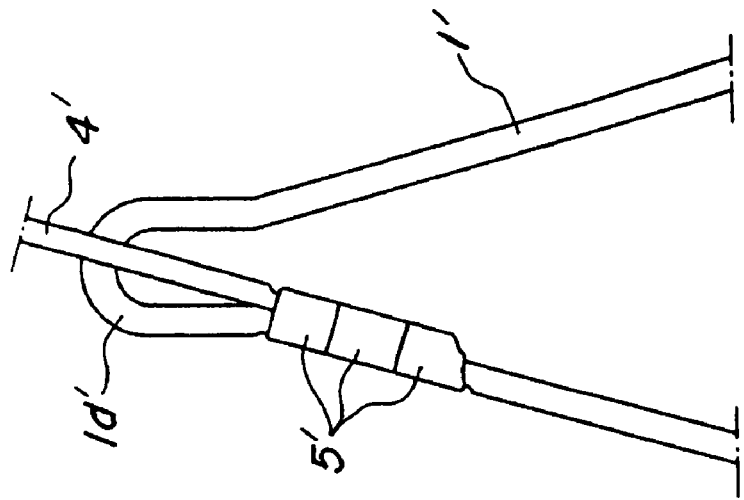
Figure 10:
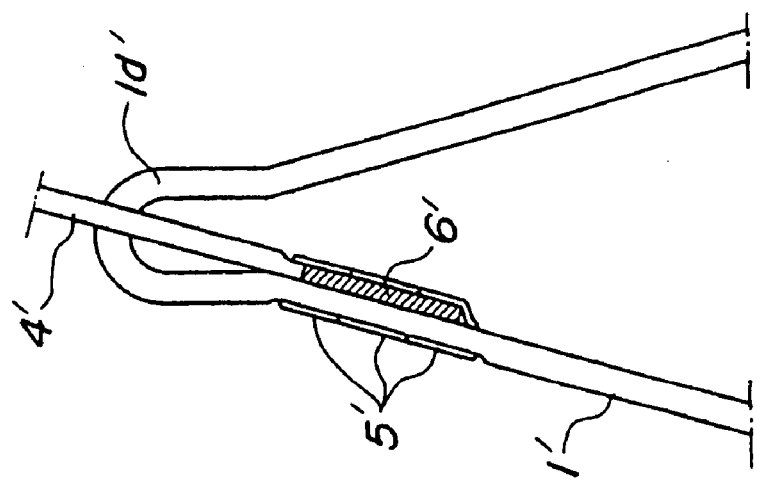

While the connection portion 5, 5A, 5B in FIGS. 1 and 2 is shown as a straight line, the connection portion shall not be limited thereto, and it may be a curved line. The above curved line stands for a line having at least one curved portion and includes a substantially S-letter-shaped line. For connecting the annular unit and the connection portion, specifically, the connection portion 5, 5A, 5B and the generally straight line portion 6, 61, 62, 63, 64 are bonded to each other by known bonding means such as welding, brazing (welding), calking, or the like. When calking is employed, the connection may be made by calking with a pipe unit to be described later. In the stent 1 of the present invention, the central curved portion 8, 8A, 8B has at least a semicircular portion as shown in FIGS. 1 to 3 (or as shown in FIGS. 8 and 10 to be discussed later), and can be in the form of a ring or the like.

In the stent 1 of the present invention, adjacent annular units are connected to each other with at least two connection portions 5, 5A, 5B above, and these connection portions are disposed (arranged) with a space between them. That is, as shown in FIGS. 1 and 2, the annular units are arranged with a space of at least one central curved portion 8, 8A, 8B (generally a space of 1 to 4 central curved portions) constituting the above zigzag patterns 7. For example, FIG. 2 shows an embodiment in which the annular units 4A and 4B are connected with the connection portions 5A and 5B, and it can be understood that two central curved portions 8A and two central curved portions 8B are arranged or placed between the connection portions 5A and 5B.

The above point will be explained further in detail. In an embodiment of the stent 1 of the present invention as shown in FIG. 1, five annular units 4A, 4B, 4C, 4D and 4E are connected with connection portions 5A, 5B. With the connection of annular units 4B and 4C, three central curved portions 8A and three central curved portions 8B are arranged between connection portions 5A and 5B ($n_3$=3) (calculated on the basis of the configuration that two central curved portions 8A and two central curved portions 8B are arranged between 4A and 4B as described above). With the connection of the annular units 4C and 4D, two central curved portions 8A and two central curved portions 8B are arranged ($n_2$=2) like 4A and 4C, and with the connection of annular units 4D and 4E, one central curved portion 8A and one central curved portion 8B are arranged ($n_1$=1).

As shown in FIG. 1, the stent 1 of the present invention has a configuration curved along the longitudinal direction thereof. Accordingly, angles ($θ_i'$) at which those lines of the annular units constituting the stent, drawn in the radius directions of the stent, cross each other, increases with an increase in the number ($n_i$) of the central curved portions 8A, 8B arranged between the connection portions 5A and 5B, that is, $n_1 < n_2 < n_3$, and thereby the relationship of $θ_1 < θ_2 < θ_3$ holds.

As described above, by adjusting the angles ($θ_i$) and the number ($n_i$), the degree of curve angle (degree of curvature) of the above adjacent annular units 4A and 4B. (4C, 4D, 4E) in the longitudinal direction of the stent can be adjusted, wherein the angles ($θ_i$) are the angles at which those lines of the annular units constituting the stent which are drawn in the radius directions of the stent cross each other and the number ($n_i$) is the number of the central curved portions 8A, 8B arranged between the connection portions 5A and 5B.

Further, FIG. 1 shows the case wherein the connection portions 5 having the same lengths each, the degree of curve angle (degree of curvature) of the above adjacent annular units 4A and 4B (4C, 4D, 4E) in the longitudinal direction of the stent can be adjusted by changing the length of connection portions 5, 5A and 5B.

While the ratio φ (=S/L) of the length S of the connection portion 5, 5A, 5B to the length L of the generally straight line portion 6, 61, 62, 63, 64 is made and shown as approximately 0.4 in FIG. 1, the above ratio is preferably made in the range of 0.1 to 2.0. When the ratio φ is less than 0.1, it is difficult to adjust the angles between the annular units 4, 4A and 4B. When the length ratio φ exceeds 2.0, undesirably, the stent may produce kinking after a long period of time or the expansion strength of the connection portions 5, 5A and 5B decreases.

In the stent 1 of the present invention, the number of the zigzag patterns may be changed as required for improving the stent in flexibility. Preferably, at least one annular unit 4A or 4B having an odd number of the zigzag patterns 7 and at least one annular unit 4A or 4B having an even number of the zigzag patterns 7 are provided, and these are combined as required for constituting the stent 1.

Preferably, in particular, the annular units having an odd number of the zigzag patterns 7 and the annular units having an even number of the zigzag patterns 7 are arranged to be adjacent to each other and alternately placed in the longitudinal direction of the stent 1.

Specifically, for example, one of the above annular units 4A and 4B adjacent to each other is constituted of an odd number (e.g., 7, 9, 11 or the like) of the zigzag patterns 7, and the other is constituted of an even number (e.g., 8, 10, 12 or the like) of the zigzag patterns 7. Alternatively, two adjacent annular units having both an odd number (7, 9, 11) of the zigzag patterns 7 and two adjacent annular units having both an even number (8, 10, 12) of the zigzag patterns 7 can be alternately arranged along the longitudinal direction of the stent 1.

In the stent 1 of the present invention, contact of the zigzag patterns of the adjacent annular units can be prevented and arranged to overlap during expansion, so that a sharp curved configuration can be secured. The reason therefor is as follows. As shown in FIGS. 1 to 3, when the stent 1 is viewed from the outermost curved line R side of the stent 1 in a state where the stent 1 has a configuration curved in the longitudinal direction of the stent 1, 1 to 4 central curved portions 8, 8A, 8B constituting the zigzag patterns 7 are arranged between the two connection portions 5, 5A, 5B between the annular units 4A and 4B adjacent to each other and are opposed to each other (see FIG. 2, when the FIG. 1 is viewed from the X side), and on the other hand, the central curved portions 8, 8A, 8B of the zigzag patterns 7 constituting one of the annular units 4A and 4B adjacent to each other and the inside spaces 9 of the zigzag patterns 7 constituting the other are arranged substantially to be opposed to each other when the stent 1 is viewed from the innermost curved line R' side of the stent 1 (see FIG. 3, when FIG. 1 is viewed from the Y side). The stent of the present invention is thus constituted, the zigzag patterns 7 can overlap, without contacting, the adjacent zigzag patterns 7 during expansion, and the configuration of the curved line R can be adjusted to take a sharper curve.

From the above viewpoint, in the stent 1 shown in FIG. 1, the annular units 4A, 4B, 4C, 4D and 4E having respectively, 9, 10, 9, 10 and 9 zigzag patterns 7 are connected.

FIG. 1 to 3 show an embodiment of the stent 1 of the present invention in which annular units 4A, 4B having an odd number of the zigzag patterns 7 and annular units 4A, 4B having an even number of the zigzag patterns 7 are adjacent to each other and arranged alternately in the longitudinal direction of the stent 1 as described above for forming a structure of the stent more adaptable to the curved portion of a diseased part, that is, an arrangement pattern of odd number . even number . odd number . even number . . . is made. The other arrangement pattern may also be employed. For example, when a diseased part (blood vessel) includes a diseased part (blood vessel) having the form of a straight line or a generally straight line, there can be preferably employed an arrangement pattern of odd number . odd number . . . and/or even number . even number . . . , or the like for that part.

Preferably, the stent 1 of the present invention is formed such that the ratio (contract ratio) of the contracted diameter of the generally tubular body, when inserted to a diseased part such as an aneurysm, or the like to the unloaded diameter of the generally annular body is between 20% to 90%. In a diseased part (blood vessel), the stent of the present invention is thus diameter-contracted as required thereby to exert a higher radial force against a diseased part, so that the initial leak of blood to a swelling wall, including the leak immediately after the treatment, can be reliably stopped. When the contract ratio is too large (less than 20%), or too small (over 90%), undesirably, the above desired radial force is not exerted.

The metal wire base material for forming the stent 1 of the present invention is not specially limited, and the stent 1 is formed from a wire made of a metal generally used, such as stainless steel such as SUS316L or the like, a superelastic alloy such as a Ti—Ni alloy or the like, titanium, a titanium alloy, tantalum, a tantalum alloy, platinum, a platinum alloy, tungsten, a tungsten alloy, or the like.

The stent made of any one of the above metals may be surface-coated with biocompatible polymer materials such as polyurethane, polyvinyl pyrrolidone, polyvinyl alcohol, or the like, with physiologically active substances such as heparin, urokinase or the like immobilized to the above coated polymer materials by chemical bonding, or with antithrombotic drugs such as argatroban, cilostazol, sarpogrelate HCl, or the like mixed to the above coated polymer materials.

The stent graft constituted of the above stent, provided by the present invention, will be explained with reference to FIGS. 5 and 6 hereinafter.

The stent graft 11 of the present invention comprises the stent 1 and a tubular member 12 made of a synthetic resin, wherein the stent being covered with the tubular member 12. Like the stent 1, the stent graft 11 is used for repairing a blood vessel damaged by a stenosis, an aneurysm or the like or used as a replacement for a hollow organ.

FIG. 5 is a schematic drawing of the stent graft 11 of the present invention, and it shows a state wherein the stent 1 shown in FIG. 1 is contracted to a size, the size with which the stent 1 inserted in a diseased part, and the stent 1 is circumferentially covered with a tubular member 12 (also called "graft") (indicated by a dotted line) made of a synthetic resin.

Figure 7:
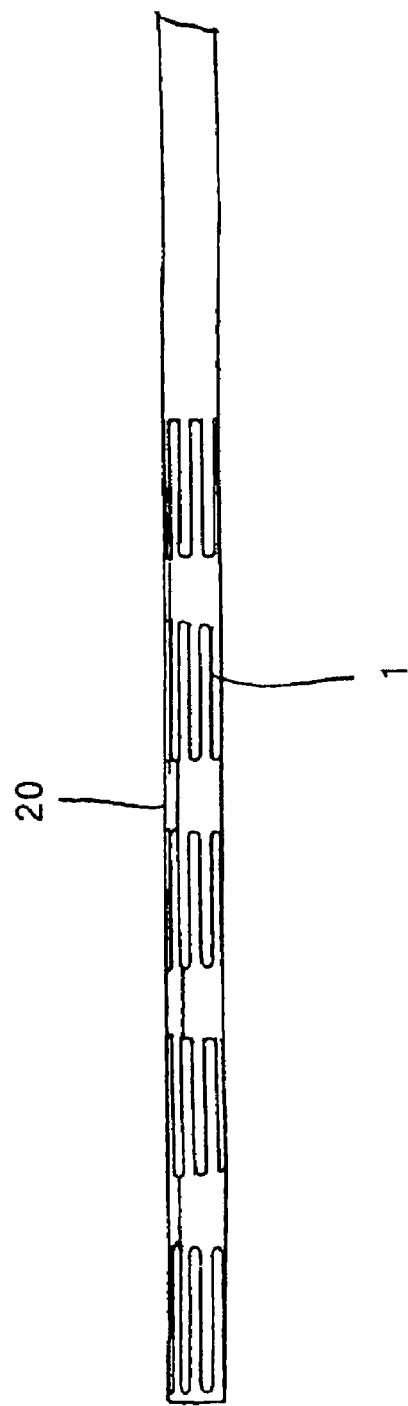

FIG. 6 is a schematic drawing showing a state where the stent 1 is loaded into a sheath 10 having a curved forward end, and FIG. 7 is a schematic drawing showing a state wherein the stent 1 is loaded in a sheath 20 having a straight-line forward end. (In addition, the tubular member (graft) made of a synthetic resin is fitted to the outside of the stent 1 and is diameter-contracted in conformity with the form of the stent 1, while FIGS. 6 and 7 omit showing its diameter-contraction).

Specifically, the stent graft 11 can be manufactured by covering the above stent 1 with the tubular member 12 made of Dacron (polyethylene terephthalate fiber, E.I. du Pont de Nemours and Company, trade name), a film made of a fluorine resin (PTFE: polytetrafluoroethylene), or the like.

In one embodiment of the stent graft, for example, a stent having a diameter of 40 mm under no load is provided and contracted to 30 mm (75%), a tubular member made of Dacron, having a diameter of 31 mm, sutured at end portion and any portion with a suture thread is covered and fixed on/to the above stent, whereby the stent graft 11 can be manufactured.

In the stent graft 11 of the present invention, the stent 1 that has a spring function and has good flexibility is covered with the tubular member 12 made of a synthetic resin in the form of a fiber or a film, so that the stent graft 11 can conform, as a stent graft, to the three-dimensional curve of a blood vessel as required.

While the annular units 4A, 4B of the stent 1 shown in FIGS. 1 to 3 have the same diameter each, both ends of the stent 1 may have different diameter(s) depending upon a diseased part (blood vessel). In this case, desirably, annular units 4A, 4B having different diameters each are combined in conformity with the form of a diseased part (blood vessel), and the stent graft 11 is manufactured in conformity with the form thereof. For example, when two ends of a diseased part have different diameters, the stent graft 11 can be adapted thereto by bringing the diameters of the annular units 4A, 4B forming both ends thereof into conformity with the form of the diseased part (blood vessel).

According to the stent, etc., of the present invention explained in detail hereinabove, the stent is designed initially and normally to be in a curved state easily adaptable to a curved blood vessel in a diseased part, so that there can be provided the stent 1 having excellent conformity to a curved portion of the main artery of a patent.

Further, the stent, etc., of the present invention can have a curved form without increasing the length of the connection portion 5, 5A, 5B between the annular units 4A and 4B, and it does not easily undergo kinking or deformation, so that it does not move even when it is anchored or left in a diseased part for a long period of time.

For the stent, etc., of the present invention, some combinations of diameters of the annular units 4, 4B and the zigzag patterns 7 are prepared or stored in advance. Consequently, then, there can be manufactured the appropriate stent 1 wherein selection with regard to positions of the annular units 4A, 4B and the connection portions 5, 5A, 5B are made as required depending upon the targeted diseased part, thereby preferable stent 1 usable for an acute or subacute case of disease can be readily provided.

The basic embodiment of the stent, etc., of the present invention has been explained hereinabove. Other working embodiment of the present invention will be explained with reference to drawings hereinafter.

Figure 9:
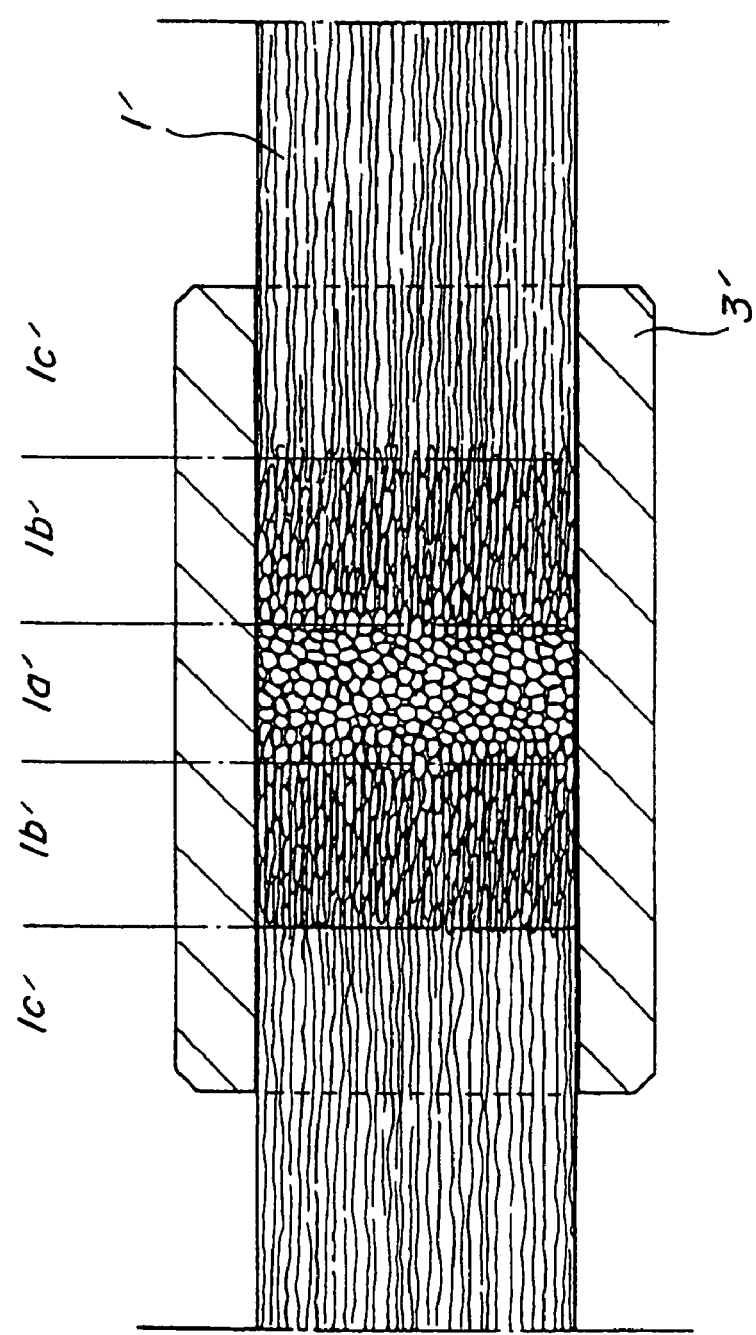
Figure 11:
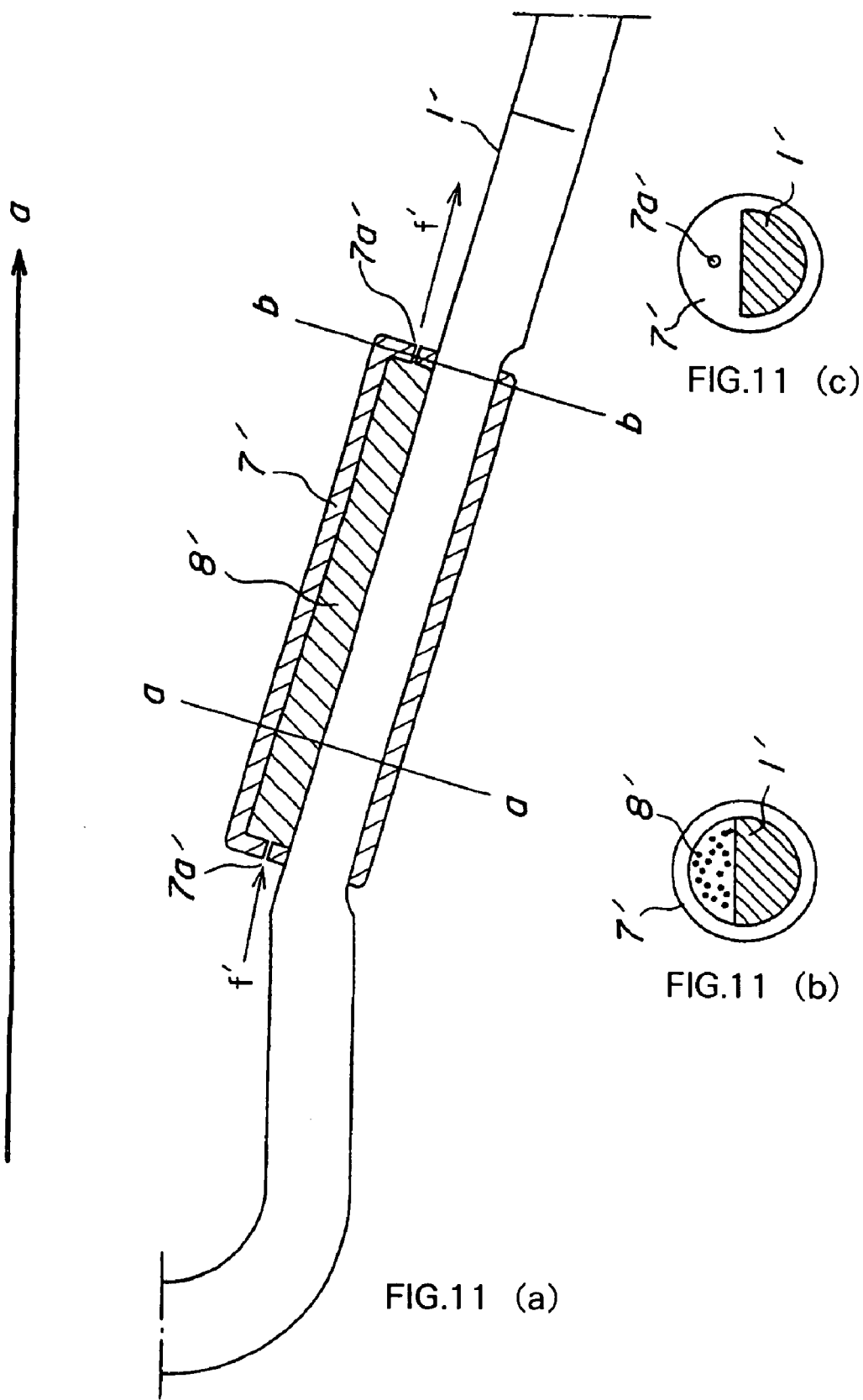
Figure 12:
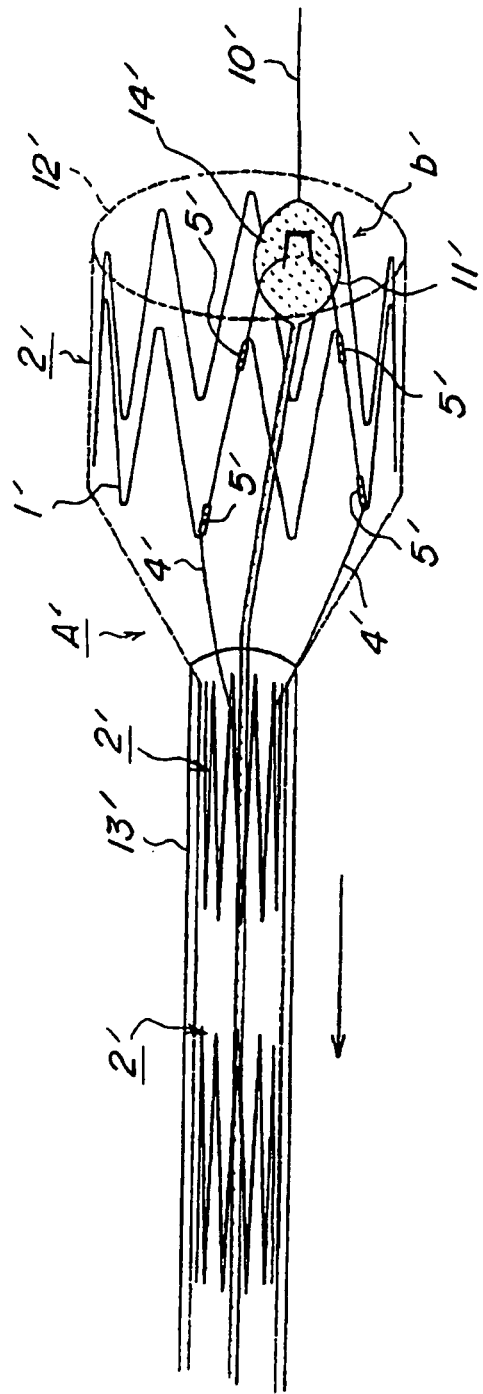
Figure 12:
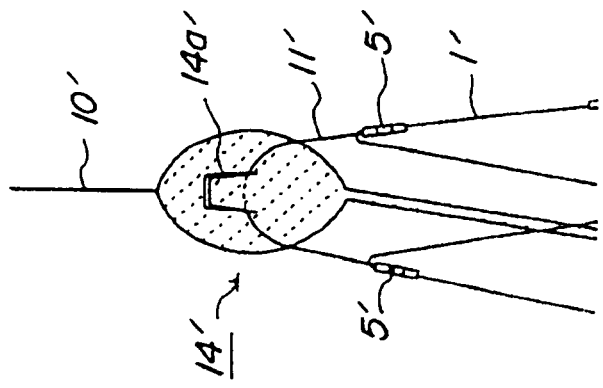

FIGS. 8 to 11 are drawings showing a stent in which a pipe unit that exhibits the function of reinforcement, sustained release of a drug, or the like is fitted to the stent main line made of a metal line wire base material. FIG. 8 is a drawing for explaining a state wherein two annular units are connected to each other with connection struts to form a stent and the connected stent is provided with pipe units. FIG. 9 is a drawing for explaining a structure of a welded portion as a change in the stent main line. FIG. 10 is a drawing for explaining a state wherein an X ray impermeable portion is protected with a pipe. FIG. 11 is a drawing for explaining a state wherein a pipe charged with a drug and sealed is attached. FIG. 12 is a drawing for explaining a state wherein a hook is connected to the stent main line with a pipe.

The other working embodiment of the present invention has a characteristic feature in that a pipe unit is fitted to the stent main line to cause the stent to exhibit the various functions of reinforcement, sustained release of a drug, and the like. The targeted stent, to which the pipe unit for imparting the above functions is most effectively applied, is naturally, and in the first principle, to the stent having a curved configuration in the longitudinal direction in a stationary or normal state as shown in FIG. 1. However, the technical feature or idea thereof is not limited thereto and can be applied to a more general stent. The following explanation therefore includes an explanation with regard to a general stent.

That is, the stent with a pipe unit, provided by the present invention, is a stent A' that is generally a tubular body comprising generally annular units 2' formed by bonding end portions of a stent main line 1' made of a metal line wire base material formed in a zigzag form and connection struts 4' connecting said annular units 2' in series, wherein a pipe unit 3' being inserted and fitted to a changed portion of the stent main line 1' and/or the connection strut 4' in said annular unit 2' and fixed to said stent main line 1', or wherein a pipe unit 5', 7' being fitted to that portion of the stent main line 1' which is provided with an element different from the stent main line 1' and/or the strut 4' in said annular unit 2', thereby causing the stent to exhibit at least one of functions for reinforcement, sustained release of a drug and marker protection. The above mentioned change of the stent main line, etc., includes a change in diameter and a change in structure, and for example, it means that site of the stent main line or the strut, at which site its diameter is reduced, for connection of strut to the stent is to be arranged along the stent main line, and a portion or site that comes to have coarse-particle-structure due to heat or thermal effect caused by welding both ends of the stent main line or welding end portions of the stent main line and that of the strut. The pipe unit is arranged and fixed to the above site for reinforcement as will be described later.

Further, the element different from the stent main line, etc., means solid substances such as an X ray impermeable portion (X ray imaging marker such as a plating, a foil, etc.) formed in the stent main line or the connection strut, or a solid drug. The pipe unit is arranged and fixed so as to be opposed or faced thereto as will be described later, so that it can prevent a plating or foil constituting the above X ray impermeable portion from coming off, and that it can prevent these substances from entering in blood stream even when the substances come off.

The stent A' shown in FIG. 8 is formed of annular units as described already. Specifically, the stent main line (wire base material made of a metal) 1' is bent in a predetermined zigzag form (zigzag patterns), and both ends of the stent main line 1' are faced and bonded to each other by welding to form an annular unit (which is, sometimes referred to as "loop") 2'. A pipe unit 3' for reinforcement is arranged in the above welded portion to reinforce it, further, a plurality of such annular units 2' (two annular units here) are arranged in series, at least two connection struts 4' and 4' are disposed between the adjacent annular units 2', the adjacent annular units (stent main lines thereof) are fixed and connected with the above connection struts 4' preferably by welding, and the welded portions are reinforced with pipe units 5'. There may be employed a constitution wherein the connection strut 4' and the stent main line 1' of the annular unit is connected to each other by calking with the pipe unit 5'.

As the stent main line 1', there is used a material such as generally provided austenitic stainless steel or a wire material of SUS316L particularly provided as a stainless steel for implants as described already. And these stainless wire material materials are subjected to cold wire drawing so that the structure thereof is extended in the form of fibers (fibrous structure), thereby causing the material to exhibit work hardening to improve its mechanical properties. The stent formed of the above material has excellent biocompatibility and has proper expandability, and, therefore, when it is released from the sheath in an intended diseased part, it easily restores the initial form. Further, the above material has strong resistance against age-deterioration, so that it is suitable for anchoring or leaving the stent in a diseased part in a human body for a long period of time.

In the present invention, the annular unit is formed by bonding end portions of the stent main line (wire base material made of a metal) made of stainless steel having excellent properties to each other by welding. In this case, however, the following problem of a decrease in the strength of the welded portion can occur.

That is, FIG. 9 is a drawing for explaining a change in the structure of metal in the welded portion of the stent main line when the end portions of the stent main line 1' formed in a zigzag form are cause to face each other and resistance-welded to form the annular unit. As shown in this Figure, in a welded region 1a' formed mainly of butt ends, the metal structure is caused to be coarse due to welding heat and comes to be granulated, and the strength thereof as a wire base material of the stent main line is greatly decreased.

Further, regions 1b' and 1b' outside the above area are affected by the welding heat to some extent, so that the metal structure thereof is caused to granulate, and a decrease in strength also occurs in these regions. Regions 1c' and 1c' outside them are regions that do not substantially suffer the heat effect of welding, and the original structure in the form of extended fibers remains intact and maintains the strength inherent to the wire base material.

In the present invention, therefore, a pipe unit 3' is arranged, for reinforcement, in those portions of the welded portion of the stent main line 1' which include the welded region 1a' as a center and the regions 1b', 1b', which suffer a relatively large decrease in strength as: compared with the areas 1c', 1c', thereby securing the strength inherent to the annular unit 2'.

Specifically, the pipe unit 3' that has a length capable of covering at least the region 1a' up to the regions 1c', 1c' on both sides thereof is inserted and fitted to the stent main line 1' as shown in FIG. 9, and in this position, both end portions of the above pipe unit 3' are calked to fix and integrate the pipe unit 3' to/with the stent main line 1. The above pipe unit 3' for reinforcement, thus applied, can reinforce that site of the metal structure which is decreased in strength by suffering from the welding heat.

The size (length) of the welded region 1a' and the regions 1b' in the annular unit 2' is not uniquely determined and takes a value that differs depending upon the diameter of the stent main line 1' used. However, the above length is not so great, and in any case, it is on the unit of several millimeters at the greatest. For example, when the stent main line 1' has a diameter of approximately 0.45 mm, generally, the total length of the region 1a' and the regions 1b' is approximately 0.7 mm. It is therefore sufficient that the pipe unit 3' has a length of approximately 1 mm. Practically, however, the pipe unit 3' may have a length of 7 mm by taking into account of a calking margin, and it is practical to use a cylindrical pipe having an outer diameter of approximately 0.65 mm and an inner diameter of approximately 0.46 mm.

While the material of the pipe unit 3' is not specially limited, it is preferred to use a pipe made of the same material as that of the stent, such as SUS316L provided as a stainless steel for implants, since it is anchored or left in a diseased part together with the stent for a long period of time.

As described above, according to the present invention, for example, an austenitic stainless steel having an extended fibrous structure, or the like, is used for the stent main line 1', and the pipe unit 3' for reinforcement is arranged and calked in a welded site of the annular unit 2' formed by welding end portions of the stent main line 1', whereby reinforcement can be made with the welded site of the above annular unit.

Meanwhile, when the stent is to be formed, the annular units are connected with the connection unit, and welding is also employed therefor, so that the same problem as above arises. Therefore, the connection portion (welded portion) of the annular unit and the connection member (connection strut) can be reinforced with a pipe unit 5' as shown in FIG. 8.

The pipe unit 5' for reinforcement, which is to reinforce the connection portion (welded portion) of the stent main line 1' constituting the annular unit 2' and the connection strut 4', is inserted and fitted to the stent main line 1' after the stent main line 1' is formed into the zigzag patterns but before the end portions are welded (before the annular unit is formed). It is therefore required to pass the pipe unit 5' through the peak portion(s) (central curved portions) 1d, of the zigzag pattern (s). The above portion 1d' has a semicircular portion as shown in FIG. 10. Preferably, the pipe unit is designed to have such small dimensions that said pipe unit can easily pass through the above peak portion 1d' with regard to its length, and a plurality of such pipe units 5' (generally, about 3 pipe units) are arranged in each connection portion.

Generally, the pipe unit 5' is preferably designed to have a length that is three times as long as the diameter of the stent main line 1' or less. According to the present inventors' finding, when the stent main line 1' has a diameter of 0.45 mm, and if the pipe unit 5' has a length of approximately 0.98 mm, working can be most smoothly carried out. On the other hand, it has been found that if the length is smaller than 0.5 mm, it is difficult to secure smooth workability.

Then, the pipe unit is fitted to that portion of the stent main line of the stent A' at which is to be provided with the element different from the connection strut, the different element being such as a drug or an X ray imaging marker, thereby the stent A' can perform the above function for marker protection, sustained release of a drug, or the like.

In the present invention, the stent is delivered to a diseased part (blood vessel) while monitoring the stent position, it is preferred to form an imaging marker such as an X ray impermeable portion 6' or the like at some part of the stent main line 1'. For obtaining a clear X ray contrast image, a metal material or inorganic material, an X ray impermeable material having a specific gravity of 8 or more, is caused to adhere or fixed to part of a long line of a zigzag pattern, a foil thereof is attached thereto, or a thin film thereof is formed thereon, as a marker. Examples of the above X ray impermeable material (marker material) include gold, silver, platinum, tungsten, barium, molybdenum, tantalum, iridium, bismuth and oxides, carbides, nitrides, borides, etc., of these.

The means of forming a thin film of any of these can be selected as required depending upon each metal, etc., and there can be applied any means such as plating, sputtering, reactive sputtering, vacuum vapor deposition, bonding of a thin film thereof (gold foil, etc.), pressure-bonding, or the like.

In the present invention, for example, it is relatively easy to apply gold plating or a gold foil to an end portion of the relatively short and generally straight-shaped connection strut 4', so that the X ray impermeable portion 6' is formed in a predetermined range (such a length that can be covered with the length of pipe unit 5') in an end portion of the connection strut 4' by plating gold.

The X ray impermeable portion 6' may be any portion so long as the position of the stent A' can be reliably monitored with X ray imaging, and particulars thereof shall not be limited. According to the finding of the present inventors, when the stent main line 1' has a diameter of 0.45 mm and the connection strut 4' has a diameter of 0.35 mm, and if a gold plate having a thickness of 2 μm is formed in a range of 3.5 mm to 4 mm, the monitoring of the position can be reliably made with X ray imaging.

In this case, the pipe unit 5' has a length of approximately 1 mm, and 5 to 6 pipe units 5' are arranged side by side by connection and calked, thereby covering of the X ray impermeable portion 6' and the connection of stent main line 1' and the strut 4' can be both provided.

When the annular units 2' are connected with the connection strut 4', the end portion of the connection strut 4' on which the X ray impermeable portion 6' is formed is arranged along the stent main line 1', and a plurality of the pipes 5' are inserted and fitted them and calked, whereby the X ray impermeable portion 6' can be covered and protected with the pipes 5'. Further, when the stent A' is anchored or left in a diseased part, the X ray impermeable portion 6' is not exposed directly to a blood flow.

When the stent A' is anchored or left in the main artery, therefore, a gold plating or a gold foil is not peeled off. Even if it should be peeled off, it does not in the least pass through the pipe unit 5' to enter a blood vessel, thereby preventing the peeled gold plating or gold foil from causing a thrombosis. When the connection strut 4' with the X ray impermeable portion 6' formed thereon is connected to the stent main line 1' constituting the annular unit 2', preferably, the position to which the gold plating or gold foil is applied is in the vicinity of the peak portion (central curved portion) 1d' of the annular unit 2' so that the passageway through which the stent A' reaches a diseased part can be reliably monitored by X ray imaging.

Another embodiment in which, as an element imparted with a function different from the stent main line 1' and the connection strut 4', a fluid drug 8' containing a powder or liquid is administered from the stent A' by sustained release, will be explained below with reference to FIG. 11.

Since a narrow blood vessel is liable to have a thrombosis, generally, an anti-thrombosis drug is externally administered. When the drug can be fitted to the stent A' inserted in a blood vessel and gradually released from the stent directly into blood at an intended place, advantageously, the effect of the drug can be more effectively produced.

When the stent A' is fitted with a drug such as an anti-thrombosis drug, a relatively long pipe unit 7' is used as shown in FIG. 11(a), a powder, preferably fluid drug 8', is charged into the pipe unit 7' and sealed, and the pipe unit is fitted and arranged to/on the stent main line 1'. As a drug 8', an optimum one is selected in advance depending upon a patient to be treated and an operation method employed and charged into the pipe unit 7'. FIG. 11(b) is a cross sectional view taken along line a-a in FIG. 11(a), and FIG. 11(c) is a cross sectional view taken along line b-b in FIG. 11(a).

Accordingly, there is provided a constitution in which the pipe unit 7' has a very small hole portion 7a' formed in a predetermined position (e.g., a position that permits a contact with blood flow, such as an end surface or a side surface), the drug comes in contact with blood, which enters and flows away through the above hole portion 7a', and the drug can be dissolved gradually in the blood and released.

The pipe unit 7' for sealing a drug therein and gradually releasing it is formed generally to be relatively long. Therefore, even when attempts are made to fit and arrange the above pipe unit 7' after the stent main line 1' is formed in zigzag patterns, it is difficult to pass the pipe unit 7' through the peak portion (central curved portion) 1d'. It is thus preferred to arrange the pipe unit 7' in the straight line portion in the vicinity of a welded area of the stent main line 1'.

Particularly, for increasing the inner volume of the pipe unit 7', preferably, the stent main line 1' is shaped in a form including a semicircular at cross section beforehand as shown in FIG. 11(b), and the pipe unit 7' is arranged in the thus shaped portion. The pipe unit 7' is fixed to the stent main line 1' by calking both ends thereof.

When the above-constituted stent A' is anchored or left in an intended diseased part, along with the blood flow in the direction of an arrow f', part of the blood flows into the pipe unit 7' through the upstream hole portion 7a' and comes in contact with the drug 8' charged therein to gradually dissolve it. And, the blood in which the drug is dissolved flows out of the downstream hole portion 7a' of the pipe unit 7' and joins the main blood flow, thereby the above drug can be gradually released into the blood. That is, when the stent is fitted with the pipe unit having a fine hole portion charged with a drug, the gradual release of the drug can be made at a desired position in a blood, particularly, in the vicinity of a diseased part.

According to the present invention, the stent A' is fitted with the pipe unit charged with a drug such as a thrombolytic agent, or the like, whereby the stent A', when anchored or left in a diseased part, can itself exhibit an action of effective DDS (Drug Delivery System) (sustained release system) without carrying out any special external blood transfusion or administration such as an injection or the like.

Finally, an embodiment in which a hook 11' for gripping a guide wire 10', which is arranged through the sheath when the stent A' is anchored in a diseased part, is arranged as an element different from the stent main line 1' and the strut 4' will be explained with reference to FIG. 12. The hook 11' is caught on a notched portion 14a' formed in a dilator 14', and when the sheath 13' is moved backward after the dilator 14' is fixed in a diseased part, the hook 11' works to discharge the stent A' housed in the above sheath 13'. The hook 11' is formed, for example, using a wire material of an austenitic stainless steel like the connection struts 4'.

As shown in FIG. 12, the stent A' is covered with a cylindrical graft 12', and the stent A' is diameter-contracted in conformity with the internal diameter of the sheath 13' and is housed in the sheath 13'. The dilator 14' is housed in the sheath 13', and further, the guide wire 10' having a top portion externally exposed is housed in the dilator 14'. And, an operation portion at hand that is not shown is operated, to fix a forward end loop 2' at an intended diseased part with the dilator 14', and in this state, the sheath 13' is withdrawn toward the operator side, thereby the stent A' is discharged from the sheath 13, expanded and anchored in the diseased part.

Concerning the hook 11', for example, one wire material made of an austenitic stainless steel is curved, both ends thereof are arranged along the stent main line 1', the pipe unit 5' is disposed, and the hook 11' is fitted to the annular unit 2' integrally with the stent main line 1' and the pipe unit 5', by simultaneously calking them.

Particularly preferably, a gold plating or gold foil is applied to those two ends of the hook 11' which are attached to the stent main line 1', thereby forming an imaging marker such as the X ray impermeable portion 6'. In this case, the X ray impermeable portion 6' can be covered and protected with the pipe unit 5' as discussed already. Further, when the hook 11' is connected to the stent main line 1' by welding, the welded portion can be covered with the pipe unit 5' and can be reinforced by calking.

In the stent of the present invention, the pipe unit is fitted and fixed to that portion of the stent main line and/or the connection strut which suffers a change in metal structure due to welding heat and is decreased in strength as explained already, thereby the thus-changed stent main line and/or connection strut can be reinforced.

Particularly, the pipe unit is arranged and fixed to such a portion of the stent main line at which metal structure comes to have coarse particles due to heat effect caused by welding ends of the stent main line, thereby this portion can be reinforced with the above pipe unit.

Further, the pipe unit is arranged and fixed to face a solid element as a function-imparting element different from the stent main line and the connection strut, for example, the X ray impermeable portion formed on the stent main line or the connection strut, thereby said fixed pipe unit can prevent the gold plating or gold foil constituting the above X ray impermeable portion from coming off, and prevent such a substance from, in the least, entering the blood flow even if it comes off.

Further, the pipe unit charged with a fluid, for example, a drug such as a liquid or powder containing an anti-thrombosis drug and sealed, is fitted and fixed to the stent main line or the connection strut, the above drug sealed therein is maintained, and hole portion(s) opened to an inside thereof is (are) formed in predetermined position(s) of the above pipe unit, thereby the drug can be dissolved in the blood flow and can be gradually released.

As described above, the pipe unit is selectively imparted with the function of protection, the function of protecting an X ray marker, the function of sustained release of a drug, or the like, thereby a multi-purpose stent can be provided.

The invention claimed is:

1. A stent, to which a tubular member made of a synthetic resin is applied to form a stent graft used in the treatment of aneurysm developed in the thoracic aorta, formed in a shape of a generally tubular body, said tubular body having a central axis, said stent having a spring function with which said tubular body is diameter-contractible toward the central axis of said tubular body, said tubular body being expandable to an initial diameter after contraction, the stent is configured to be loaded and housed in a sheath and is configured to be delivered to and placed at a diseased part of a blood vessel with aneurysm in danger of burst to be treated, wherein:

(A) before the stent is inserted in the sheath, said tubular body is composed of a plurality of annular units, arranged or extended in a longitudinal direction of the stent and forming a preliminary and innate curved configuration of the stent, (i) the plurality of annular units comprises a plurality of generally V-letter-shaped zigzag patterns having at least one central curved portion and generally straight line portions substantially same in length on both sides of the central curved portion, the V-letter shaped zigzag patterns being formed by repeatedly bending a portion between two ends of a wire base material made of a metal, the plurality of zigzag patterns are arranged to surround the central axis of the stent, at least one annular unit is formed by bonding end portions of said wire metal at least in one portion, the plurality of annular units are connected together by a plurality of connection struts, (ii) adjacent annular units with circular cross-sectional shape, are connected with at least two of said connection struts having substantially straight line shape, (iii) said at least two connection struts which connect adjacent annular units are separate and disconnected from at least two other connection struts that connect different adjacent annular units, (iv) said curved configuration is made in accordance with the curve of the blood vessel to which the stent is to be placed, (v) wherein said at least two connection struts are disposed at a first spacing from each other, and said at least two other connection struts are disposed at a second spacing from each other greater than the first spacing, and said generally straight line portions of the zigzag patterns are formed at a connection angle Ø of 0°+30° with said plurality of connection struts to form the curved configuration of the stent, while said substantially straight connection struts all remain its straight line shape when the stent is in the curved configuration, (B) when the stent is inserted in the sheath, said stent is contracted toward the central axis of the stent and is elongated in a form of a generally straight line along the longitudinal direction of the stent, whereby the stent is loaded and housed in the sheath in the form of a generally straight line, and (C) said stent, in the form of stent graft, being loaded and housed in the sheath in the form of a generally straight line, is configured to be inserted into the diseased part of the blood vessel together with the sheath, released from the sheath, and radially, outwardly expand after release, to restore and maintain the preliminary and innate bent configuration curved along the longitudinal direction of the stent, thereby fitting smoothly to the curvature of the blood-vessel to be placed, said stent in the form of stent graft is thus placed within the blood vessel with developed aneurysm thereby forming an artificial blood vessel, which allows blood flow through and prevents the blood pressure from exerting directly on the weakened wall of aneurysm thereby keeping it from bursting.

2. The stent as recited in claim 1, wherein (i) the at least two connection struts having substantially same lengths, the connection struts thereby forming connection portions, wherein, (ii) said at least two connection struts are disposed apart at an interval or spacing with each other and in said interval or spacing between each said at least two connection struts, there are disposed at least one V-letter-shaped zigzag pattern having one central curved portion constituting the zigzag patterns (iii) and the number of the provided central curved portion constituting the zigzag pattern between said at least two connection struts are so varied as to form the preliminary and innate curved configuration, (iv) wherein the disposing of the at least two connection struts is made in a manner that the greater the number of the central curved portion constituting the V-letter-shaped zigzag pattern between the two connection struts, the greater the degree of curve made by said adjacent circular annular units.

3. The stent as recited in claim 2, wherein the annular units has an odd number of the zigzag patterns and the annular units having an even number of the zigzag patterns are disposed to be adjacent to each other and arranged alternately along the longitudinal direction of the stent.

4. The stent as recited in claim 2, wherein the connection portions or struts each have a length (S) and the generally straight line portions of the V-letter shaped zig-zag pattern each have a length (L), and wherein the connection portions and the generally straight line portions have a ratio of length (φ =S/L) of 0.1 to 2.0.

5. The stent as recited in claim 2, wherein the at least one central curved portion has at least a semicircular portion.

6. The stent as recited in claim 1, wherein said stent has at least one annular unit having an odd number of zigzag patterns and at least one annular unit having an even number of zigzag patterns.

7. The stent as recited in claim 1, wherein, in a state where the stent maintains the preliminary and innate curved configuration curved along the longitudinal direction of the stent, at least 1 to 4 central curved portions constituting the V-letter shaped zigzag patterns of adjacent annular units are arranged to be substantially opposed to each other between two connection portions or connection struts between two adjacent annular units when viewed from an outermost curved line side of the stent, and the central curved portions constituting the V-letter shaped zigzag patterns constituting one of the adjacent annular units and inside spaces of the V-letter shaped zigzag patterns of the other of the adjacent annular units are disposed so that said central curved portions constituting the V-letter shaped zigzag pattern and said inside spaces are substantially facing each other when viewed from an innermost curved line side of said stent.

8. The stent as recited in claim 1, wherein the generally tubular body under no load is contracted in diameter by 20% to 90% when said tubular body is inserted into a diseased part.

9. The stent as recited in claim 1, wherein the stent is composed of a wire base material made of a metal, and a pipe unit being fitted to the wire base material for reinforcement, marker protection or sustained release of a drug.

10. The stent as recited in claim 1, to which a tubular member made of a synthetic resin is applied to form a stent graft used in the treatment of aneurysm developed in the thoracic aorta, comprising:

a generally tubular body having a preliminary and innate curved configuration formed prior to placement in the blood vessel, the preliminarily and innate curved configuration being a curved configuration along the longitudinal direction of said stent in accordance with a curvature of a blood-vessel, and said stent being configured to maintain the curved configuration when the stent is not inserted in a sheath, wherein said generally tubular body includes annular units formed by bonding end portions of a stent main line made of a metal line wire base material formed in a zigzag form and connection struts connecting said annular units in series, and wherein (i) a pipe unit is fitted by insertion to a changed portion of the stent main line or the connection struts in said annular unit, said changed portion being a change in diameter of the main line or the connection struts or a change in composition of the main line or connection struts for reinforcement, or (ii) a pipe unit is fitted to a portion of the stent main line provided with an element different from the stent main line or the connection struts in said annular unit, said different element being X-ray-impermeable part or solid portion of a drug, for marker protection, or sustained release of the drug.

11. The stent as recited in claim 1, wherein said body has a generally circular cross-sectional shape when in said expanded state.

12. The stent as recited in claim 1, wherein said body has a generally circular cross-sectional shape when in said contracted state.

13. A stent graft, used in the treatment of aneurysm developed in the thoracic aorta, comprising a stent and a tubular member made of a synthetic resin covering said stent, wherein the stent is formed in a shape of a generally tubular body, said tubular body having a central axis, said stent having a spring function with which said tubular body is diameter-contractible toward the central axis of said tubular body, said tubular body being expandable to an initial diameter after contraction, the stent graft is configured to be loaded and housed in a sheath and is configured to be delivered to and placed at a diseased part of a blood vessel with aneurysm in danger of burst to be treated, wherein:

(A) before the stent is inserted in the sheath, said tubular body is composed of a plurality of annular units, arranged or extended in a longitudinal direction of the stent and forming a preliminary and innate curved configuration, (i) the plurality of annular units comprises a plurality of generally V-letter-shaped zigzag patterns having at least one central curved portion and generally straight line portions substantially same in length on both sides of the central curved portion, the V-letter shaped zigzag patterns being formed by repeatedly bending a portion between two ends of a wire base material made of a metal, the plurality of zigzag patterns are arranged to surround the central axis of the stent, at least one annular unit is formed by bonding end portions of said wire metal at least in one portion, the plurality of annular units are connected together by a plurality of connection struts, (ii) adjacent annular units with circular cross-sectional shape are being connected with at least two of said connection struts having substantially straight line shape, (iii) said at least two connection struts which connect adjacent annular units are separate and disconnected from at least two other connection struts that connect different annular units, (iv) said curved configuration is made in accordance with the curve of the blood vessel to which the stent in the form of stent graft is to be placed, (v) wherein said at least two connection struts are disposed at a first spacing from each other, and said at least two other connection struts are disposed at a second spacing from each other greater than the first spacing, and said generally straight line portions of the zigzag patterns are formed at a connection angle Ø of 0°+30° with said plurality of connection struts to form the curved configuration of the stent, while said substantially straight connection struts all remain its straight line shape when the stent is in the curved configuration, (B) when the stent in the form of stent graft is inserted in the sheath, said stent graft is contracted toward the central axis of the stent and is elongated in a form of a generally straight line along the longitudinal direction of the stent when the stent graft is inserted into the sheath, whereby the stent graft is loaded and housed in the sheath in the form of a generally straight line, and (C) (i) said stent graft, being loaded and housed in the sheath in the form of a generally straight line, is configured to be inserted into the diseased part of the blood vessel together with the sheath, released from the sheath, (ii) and radially, outwardly expand after release, (iii) to restore and maintain the preliminary and innate curved configuration curved along the longitudinal direction of the stent, thereby fitting smoothly to the curvature of the blood-vessel to be placed, said stent graft is thus placed within the blood vessel with developed aneurysm thereby forming an artificial blood vessel, which allows blood to flow through and prevents the blood pressure from exerting directly on the weakened wall of aneurysm thereby keeping it from bursting.

14. The stent graft as recited in claim 13 used in the treatment of aneurysm developed in the thoracic aorta, comprising a stent and a tubular member made of a synthetic resin covering said stent, wherein said stent is in a form of a generally tubular body having a preliminary and innate curved configuration formed prior to placement in the blood vessel, the preliminarily and innate curved configuration being a curved configuration along a longitudinal direction of said stent in accordance with a curvature of a blood-vessel, and said stent being configured to maintain the curved configuration when the stent is not inserted in a sheath, wherein said generally tubular body includes annular units formed by bonding end portions of a stent main line made of a metal line wire base material formed in a zigzag form and connection struts connecting said annular units in series, and wherein (i) a pipe unit is fitted by insertion to a changed portion of the stent main line or the connection struts in said annular unit, said changed portion being a change in diameter of the main line or the connection struts or a change in composition of the main line or connection struts for reinforcement, or (ii) a pipe unit is fitted to a portion of the stent main line provided with an element different from the stent main line or the connection struts in said annular unit, said different element being X-ray-impermeable part or solid portion of a drug, for marker protection, or sustained release of the drug.

* * * * *